US009759906B2

(12) United States Patent
Quin

(10) Patent No.: US 9,759,906 B2
(45) Date of Patent: Sep. 12, 2017

(54) SCULPTURAL IMAGING WITH OPTICAL TILES

(71) Applicant: QUIN MEDIA ARTS AND SCIENCES INC., Vancouver (CA)

(72) Inventor: Roderick Thomas Quin, Vancouver (CA)

(73) Assignee: QUIN MEDIA ARTS AND SCIENCES INC., Vancouver (CA)

( * ) Notice: Subject to any disclaimer, the term of this patent is extended or adjusted under 35 U.S.C. 154(b) by 299 days.

(21) Appl. No.: 14/477,202

(22) Filed: Sep. 4, 2014

(65) Prior Publication Data

US 2015/0043096 A1    Feb. 12, 2015

Related U.S. Application Data

(63) Continuation of application No. 13/543,674, filed on Jul. 6, 2012, now Pat. No. 8,837,034, which is a continuation of application No. 11/570,589, filed as application No. PCT/CA2005/000972 on Jun. 21, 2005, now Pat. No. 8,218,227.

(Continued)

(51) Int. Cl.
| | |
|---|---|
| G02B 5/08 | (2006.01) |
| G02B 26/02 | (2006.01) |
| G09F 9/37 | (2006.01) |
| G09F 19/14 | (2006.01) |
| G06F 19/14 | (2011.01) |
| B44F 1/02 | (2006.01) |
| B44F 7/00 | (2006.01) |

(52) U.S. Cl.
CPC ............... *G02B 26/02* (2013.01); *B44F 1/02* (2013.01); *B44F 7/00* (2013.01); *G06F 19/14* (2013.01); *G09F 9/375* (2013.01); *G09F 19/14* (2013.01); *Y10T 29/49* (2015.01)

(58) Field of Classification Search
CPC ... B60R 1/082; B44F 7/00; B44F 1/02; G02B 26/02; G06F 19/14; G09F 9/375; G09F 19/14; Y10T 29/49
USPC ....... 359/290, 291, 292, 295, 298, 220, 223, 359/224, 320, 323, 851
See application file for complete search history.

(56) References Cited

U.S. PATENT DOCUMENTS

| | | | |
|---|---|---|---|
| 5,633,755 | A | 5/1997 | Manabe et al. |
| 6,042,241 | A | 3/2000 | Lengyel |

(Continued)

FOREIGN PATENT DOCUMENTS

| | | |
|---|---|---|
| JP | 8-23499 A | 1/1996 |
| WO | 02/079854 A2 | 10/2002 |

OTHER PUBLICATIONS

International Search Report for PCT/CA2005/000972, International Searching Authority, Oct. 13, 2005.

(Continued)

*Primary Examiner* — Tuyen Tra

(74) *Attorney, Agent, or Firm* — Norton Rose Fulbright Canada LLP

(57) ABSTRACT

Structures for representing images comprise a plurality of tile elements which, when illuminated by a light source, each direct an amount of light toward an observer at a viewing location dependent on their orientation angles. The orientation angles of each tile element may be selected based on a characteristic of a corresponding pixel of an image, such that the observer sees a representation of that image created by the varying amount of light directed to the viewing location by the tile elements.

19 Claims, 17 Drawing Sheets

Related U.S. Application Data

(60) Provisional application No. 60/582,055, filed on Jun. 23, 2004.

(56) References Cited

U.S. PATENT DOCUMENTS

| | | | |
|---|---|---|---|
| 6,154,302 | A | 11/2000 | Yagi et al. |
| 6,243,059 | B1 | 6/2001 | Greene et al. |
| 6,252,608 | B1 | 6/2001 | Snyder et al. |
| 6,262,696 | B1 | 7/2001 | Seraphim et al. |
| 6,552,734 | B1 | 4/2003 | Rozin |
| 6,553,138 | B2 | 4/2003 | Rozin |
| 6,570,578 | B1 | 5/2003 | Smirnov et al. |
| 6,597,363 | B1 | 7/2003 | Duluk, Jr. et al. |
| 6,624,823 | B2 | 9/2003 | Deering |
| 6,712,473 | B2 | 3/2004 | Kurematsu |
| 6,829,092 | B2 | 12/2004 | Amm et al. |
| 6,857,751 | B2 | 2/2005 | Penn et al. |
| 6,956,687 | B2 | 10/2005 | Moon et al. |
| 7,184,192 | B2 | 2/2007 | Sandstrom |
| 7,359,103 | B2 | 4/2008 | Kimura |
| 7,787,170 | B2 | 8/2010 | Patel et al. |
| 7,869,061 | B2 | 1/2011 | Sato et al. |
| 8,218,227 | B2 | 7/2012 | Quin |
| 8,837,034 | B2 | 9/2014 | Quin |

OTHER PUBLICATIONS

"Wooden Mirror"—Daniel Rozin (http://fargo.itp.tsoa.nyu.edu/~danny/mirror.html).

English translation of Office Action dated Mar. 14, 2008 issued by The Patent Office of the People's Republic of China against corresponding Chinese Application No. 200580020785.8.

Sadler, Arthur, "Paper Sculpture", 3rd ed., London: Blandford Press Limited, 1954, p. 26.

Yamada, Sadami and Kiyotada Ito, "New Dimensions in Paper Craft", Tokyo: Japan Publications Trading Company, 1966, pp. 76-77.

Prior Art Submission to the Canadian Intellectual Property Office pursuant to Section 34 of the Patent Act, against corresponding Canadian Patent Application No. 2578203 dated Oct. 21, 2012.

SCULPTURAL IMAGING WITH OPTICAL TILES

REFERENCE TO RELATED APPLICATIONS

This application is a Continuation of U.S. patent application Ser. No. 13/543,674, which is a Continuation of U.S. patent application Ser. No. 11/570,589, which is a 371 of International Patent Application No. PCT/CA2005/000972 filed Jun. 21, 2005, which claims priority from U.S. provisional patent application No. 60/582,055 filed Jun. 23, 2004, all of which are hereby incorporated by reference herein.

TECHNICAL FIELD

The invention relates to structures for representing images, and particularly to structures comprising a plurality of tile elements which reflect or refract light.

BACKGROUND

Images are often represented by applying paint or ink to a two dimensional surface. Displays having such images may be readily produced, but are not visually dynamic.

Artist Daniel Rozin developed an apparatus for representing images known as the "Wooden Mirror", which is described at http://fargo.itp.tsoa.nyu.edu/~danny/mirror.html. The Wooden Mirror comprises a plurality of pieces of wood, each of which is connected to a servo motor and can be tilted about thirty degrees up and down. If the Wooden Mirror is lit from above the wood pieces which are tilted upwards appear brighter and wood pieces which are tilted downward appear darker.

Texas Instruments™ Incorporated has developed Digital Light Processing™ technology which employs digital micro-mirror devices (DMDs). As disclosed in U.S. Pat. No. 6,857,751 to Penn et al., a DMD "is an electromechanical device comprising an array of thousands of tilting mirrors. Each mirror may tilt plus or minus ten degrees for the active "on" state or "off" state. To permit the mirrors to tilt, each mirror is attached to one or more hinges mounted on support posts, and spaced by means of an air gap over underlying control circuitry."

The foregoing examples of the related art and limitations related thereto are intended to be illustrative and not exclusive. Other limitations of the related art will become apparent to those of skill in the art upon a reading of the specification and a study of the drawings.

SUMMARY OF THE INVENTION

The following embodiments and aspects thereof are described and illustrated in conjunction with systems, tools and methods which are meant to be exemplary and illustrative. In various embodiments, one or more of the above-described problems have been reduced or eliminated, while other embodiments are directed to other improvements.

One aspect of the invention provides a structure for representing a visual pattern having a plurality of areas with different brightnesses. The structure comprises a plurality of tile elements held in a fixed relationship to one another. Each of the tile elements comprises a generally planar surface inclined at an inclination angle with respect to a reference plane. Each of the tile elements corresponds to an area of the visual pattern and has an orientation angle with respect to a reference direction. The orientation angle defined between projections, on the reference plane, of a line normal to the generally planar surface, and a line parallel to the reference direction. The orientation angle is determined by the brightness of the corresponding area of the visual pattern.

Another aspect of the invention provides a structure for representing an image having a plurality of pixels. The structure comprises a plurality of tile elements held in a controlled relationship to one another. Each of the tile elements comprises a generally planar surface inclined at an inclination angle with respect to a reference plane. Each of the tile elements corresponds to at least one pixel of the image and has an orientation angle with respect to a reference direction. The orientation angle defined between projections, on the reference plane, of a line normal to the generally planar surface, and a line parallel to the reference direction. The orientation angle is determined by a characteristic of the corresponding at least one pixel. The structure also comprises a plurality of actuators for dynamically varying the orientation angles of the tile elements under control of a control system. Each actuator is coupled to one of the tile elements such that each tile element is moveable to have any one of a plurality of different orientation angles.

Another aspect of the invention comprises a method of representing an image having a plurality of pixels. The method comprises forming a plurality of tile elements held in a controlled relationship to one another, each of the plurality of tile elements corresponding to at least one of the plurality of pixels and having a generally planar surface, determining an incident light direction, and, orienting each tile element such that the generally planar surface is inclined at an inclination angle with respect to a reference plane, and such that a projection of a line normal to the generally planar surface on the reference plane and a projection of the incident light direction on the reference plane define an orientation angle. The orientation angle of each tile element is determined by a characteristic of the corresponding at least one pixel.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive. In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

The invention provides structures for representing images. Structures according to the invention comprise a plurality of tile elements which, when illuminated by a light source, each direct an amount of light toward an observer at a viewing location dependent on the orientation angles of respective tile elements relative to the light source. The orientation angles of each tile element may be selected based on a characteristic of a corresponding pixel of an image, such that the observer sees a representation of that image created by the varying amount of light directed to the viewing location by the tile elements.

In some embodiments, the invention provides a structure for reflecting light incident on a front side thereof. The structure comprises a substrate having plurality of tile elements coupled thereto. The tile elements may each comprise a reflective tile having a generally planar surface inclined at an acute angle with respect to the substrate. Each tile element may correspond to one of a plurality of pixels of an image. The tile elements may be oriented with respect to the light incident on the structure such that tile elements which correspond to brightest ones of the image pixels reflect a maximum amount of light toward the viewing location, and tile elements which correspond to least bright ones of the image pixels reflect a minimum amount of light toward the viewing location.

Figure 1:
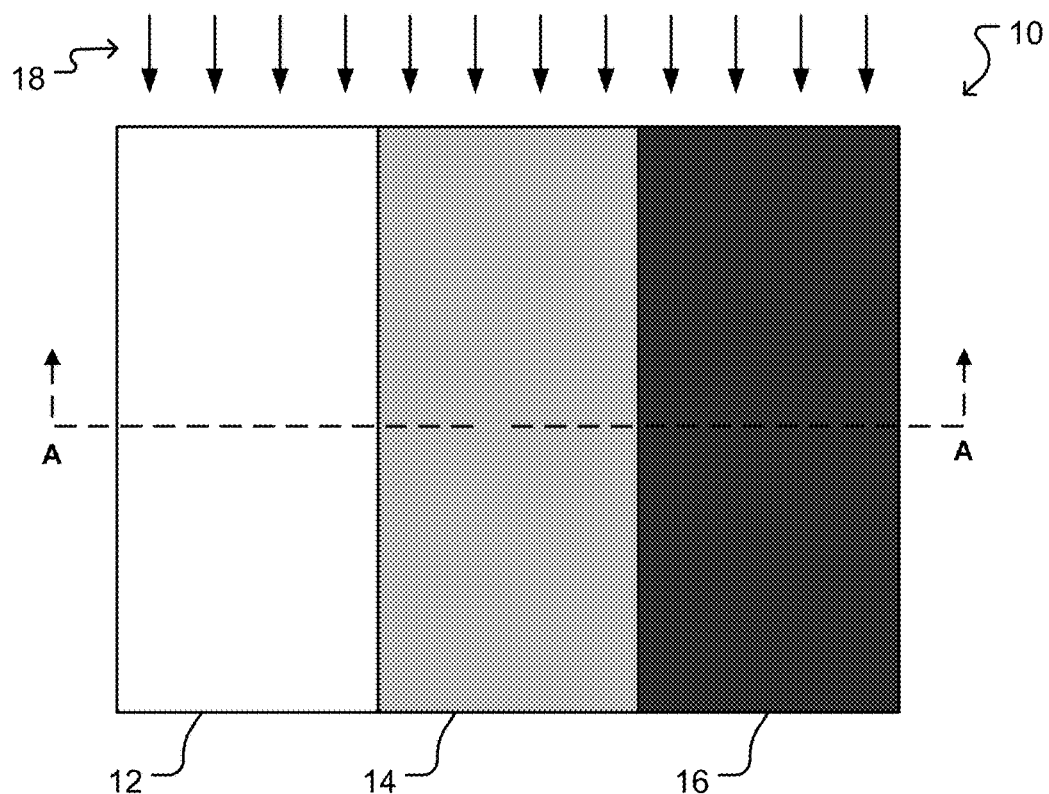
FIG. 1 schematically depicts a structure for representing an image according to one embodiment of the invention.
Figure 2:
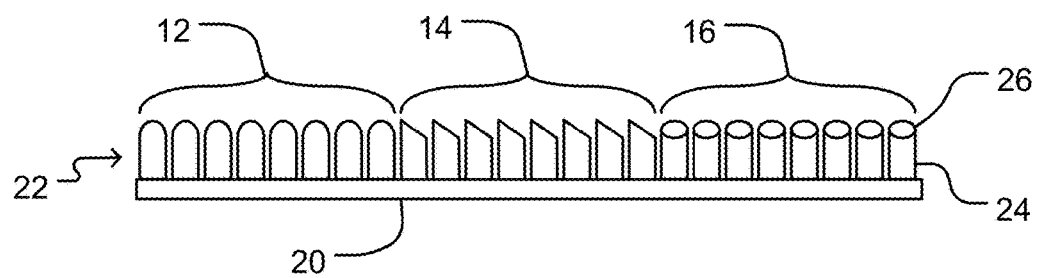
FIG. 2 is a sectional view taken along line A-A of FIG. 1.
Figure 3:
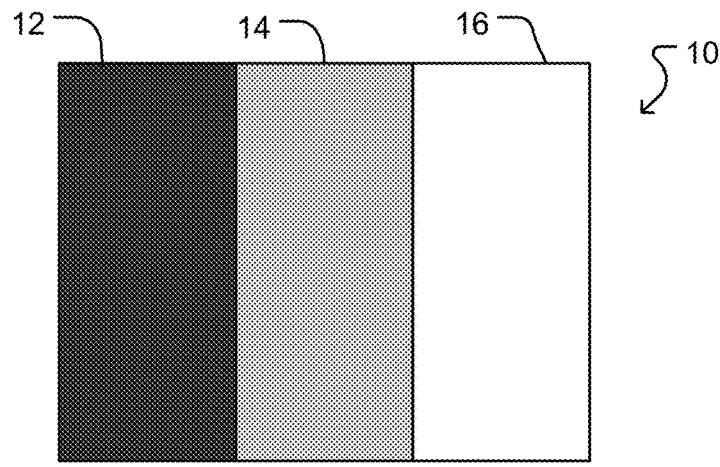
FIGS. 3 to 5 show the structure of FIG. 1 with light incident thereon from different directions.
Figure 4:
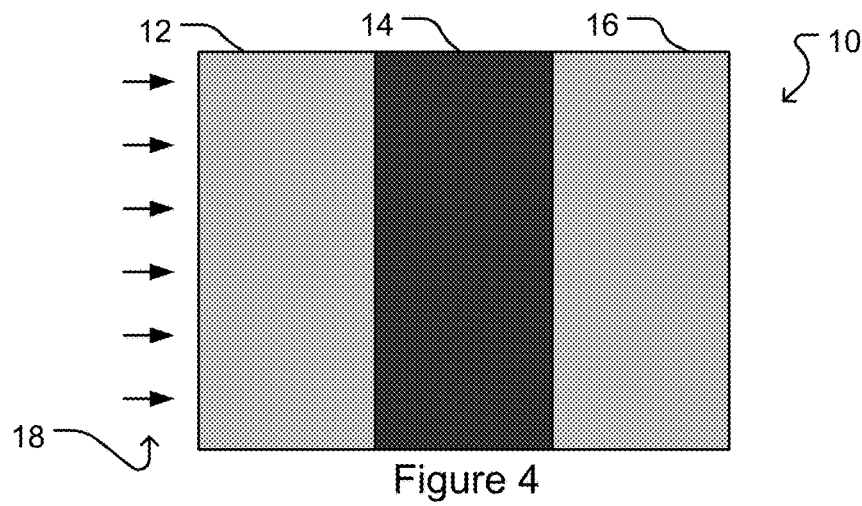
Figure 5:
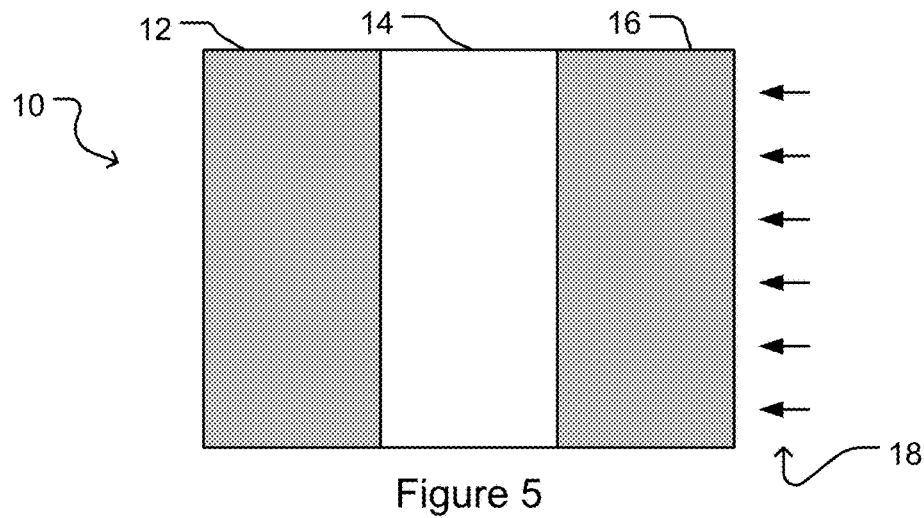

FIG. 1 shows a structure 10 according to one embodiment of the invention for representing an image in the form of a simple three-striped visual pattern. FIG. 2 is a sectional view of structure 10 taken along line A-A of FIG. 1. FIGS. 3 to 5 show the appearance of the three-striped pattern of the FIG. 1 example when structure 10 is illuminated from different directions. Structure 10 displays an image having three regions 12, 14 and 16, and is illuminated by light incident on the front of structure 10 in a direction indicated by arrows 18. In the FIG. 1 example, arrows 18 are pointing down, meaning that light is incident on structure 10 from a position generally in front of and above structure 10.

Structure 10 comprises a substrate 20 having a plurality of tile elements 22 coupled thereto. Tile elements 22 may be constructed from a material which reflects light. In the embodiment of FIGS. 1 and 2, tile elements 22 comprise cylindrical protrusions 24, each having a sheared end surface 26 inclined at an angle with respect to a reference plane (referred to as the "inclination angle"). In the embodiment of FIGS. 1 and 2, the reference plane is parallel to the surface of substrate 20, and surfaces 26 all have inclination angles of about 30 degrees. However, it is to be understood that surfaces 26 could have different inclination angles, and not all surfaces 26 need to have the same inclination angle.

Figure 29:
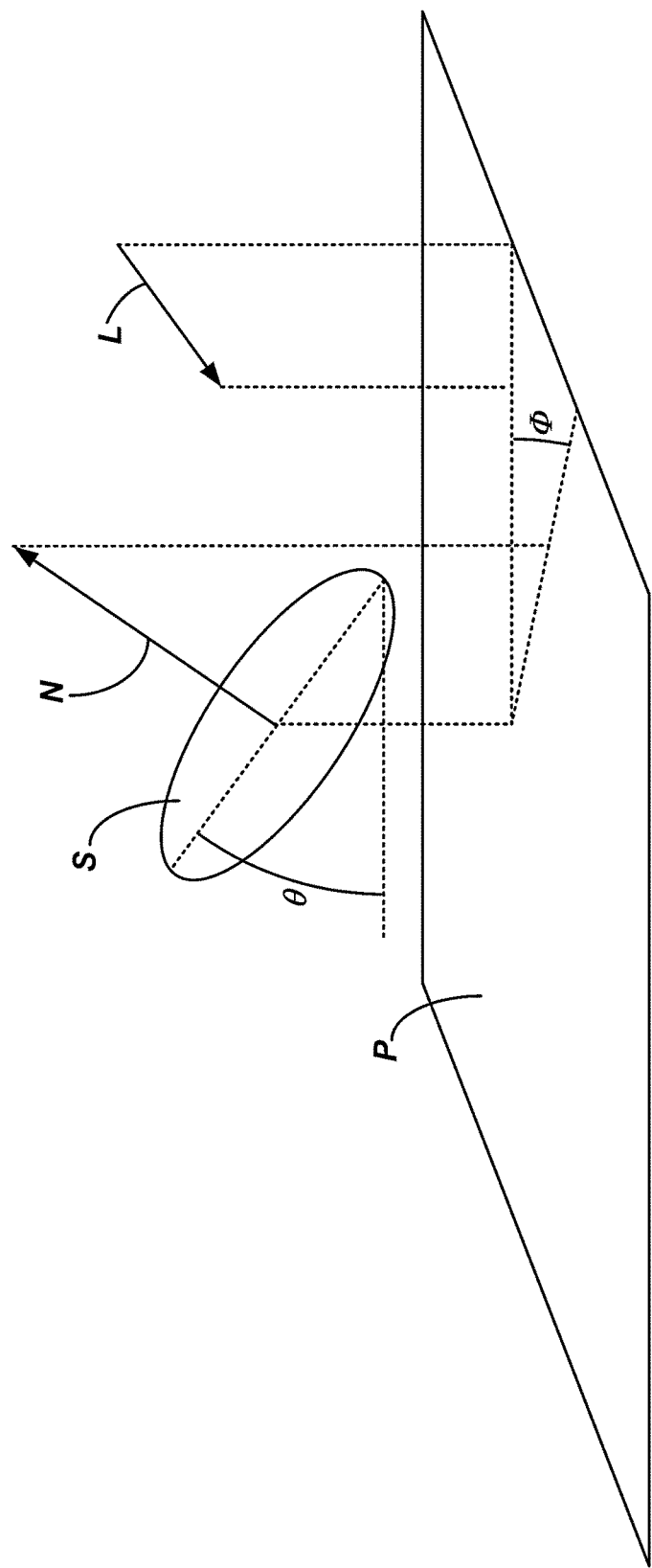
FIG. 29 illustrates the geometry of a tile element with respect to a reference plane.

Each tile element 22 is oriented such that a projection of a line normal to surface 26 on the reference plane (i.e., the surface of substrate 20) forms an angle with a projection of line parallel to a reference direction (i.e., the direction from which light is incident on structure 10) on the reference plane. This angle is referred to herein as the "orientation angle" of each tile element 22. FIG. 29 illustrates the geometry of a tile element having a surface S, an inclination angle θ and an orientation angle φ with respect to a reference plane P and incident light L. The line normal to surface S is identified by reference character N.

Surfaces 26 reflect light in an amount which varies depending on the orientation angles of tile elements 22. In the embodiment of FIGS. 1 and 2, surfaces 26 in region 12 face upwardly (i.e., the projections of the line normal to surface 26 and the direction from which light is incident on structure 10 on the reference plane are parallel and pointing in the same direction, which corresponds to an orientation angle of zero degrees), surfaces 26 in region 14 face to the right (i.e., an orientation angle of ninety degrees), and surfaces in region 16 face downwardly (i.e., an orientation angle of one hundred eighty degrees). Thus, tile elements 22 in region 12 appear brightest, because the associated surfaces 26 reflect the most light. Tile elements 22 in region 14 appear intermediately bright, because the associated surfaces 26 reflect an intermediate amount of light. Tile elements in region 16 appear the least bright, because the associated surfaces 26 reflect the least light.

As can be seen in FIGS. 3, 4 and 5, changing the direction from which light is incident on structure 10 changes the appearance of structure 10. In FIG. 3, light is incident on structure 10 from a position generally in front of and below structure 10, and region 12 is the least bright and region 16 is the most bright (i.e., structure 10 appears to display a negative of the image shown in FIG. 1). This is because the orientation angle of each tile element 22 in region 12 is one hundred eighty degrees relative to the direction from which light is incident on structure 10 and the orientation angle of each tile element 22 in region 16 is zero degrees relative to the direction from which light is incident on structure 10 in FIG. 3.

In FIG. 4, light is incident on structure 10 from a position generally in front of and to the left of structure 10, and regions 12 and 16 are intermediately bright, and region 14 is the least bright. This is because the orientation angle of each tile element 22 in regions 12 and 16 is ninety degrees relative to the direction from which light is incident on structure 10, and the orientation angle of each tile element 22 in region 14 is one hundred eighty degrees relative to the direction from which light is incident on structure 10 in FIG. 4.

In FIG. 5, light is incident on structure 10 from a position generally in front of and to the right of structure 10, and regions 12 and 16 are intermediately bright, and region 14 is the most bright (i.e., structure 10 appears to display a negative of the image shown in FIG. 4). This is because the orientation angle of each tile element 22 in regions 12 and 16 is ninety degrees relative to the direction from which light is incident on structure 10, and the orientation angle of each tile element 22 in region 14 is zero degrees relative to the direction from which light is incident on structure 10 in FIG. 4.

Structure 10 may be used to represent an image having the same resolution as structure 10 (i.e., the same number of pixels as the number of tile elements 22 of structure 10) by selecting the inclination and orientation angles of each tile element 22 based on a characteristic of a corresponding pixel of the image. For example, the incline and orientation angles of each tile element 22 may be selected based on the brightness of the corresponding pixel. Also, images having a different resolution than structure 10 may be converted into corresponding images having the same resolution as structure 10 by known conversion methods. Alternatively, each tile element 22 could correspond to a plurality of pixels of the image, or a plurality of tile elements 22 could correspond to a single pixel of the image.

As noted above, images represented by structures such as structure 10 may appear different when illuminated by light from different directions. Also, such images may appear different when viewed from different viewing locations, since the relative amount of surface area of each tile element 22 facing the viewer depends on the position of the viewer. Even if a structure such as structure 10 is illuminated from a direction perpendicular to the reference plane, a viewer may be able to see the image represented by structure 10 from certain viewing locations due to the relative amount of surface area of tile elements 22 facing toward the viewer.

Figure 6A:
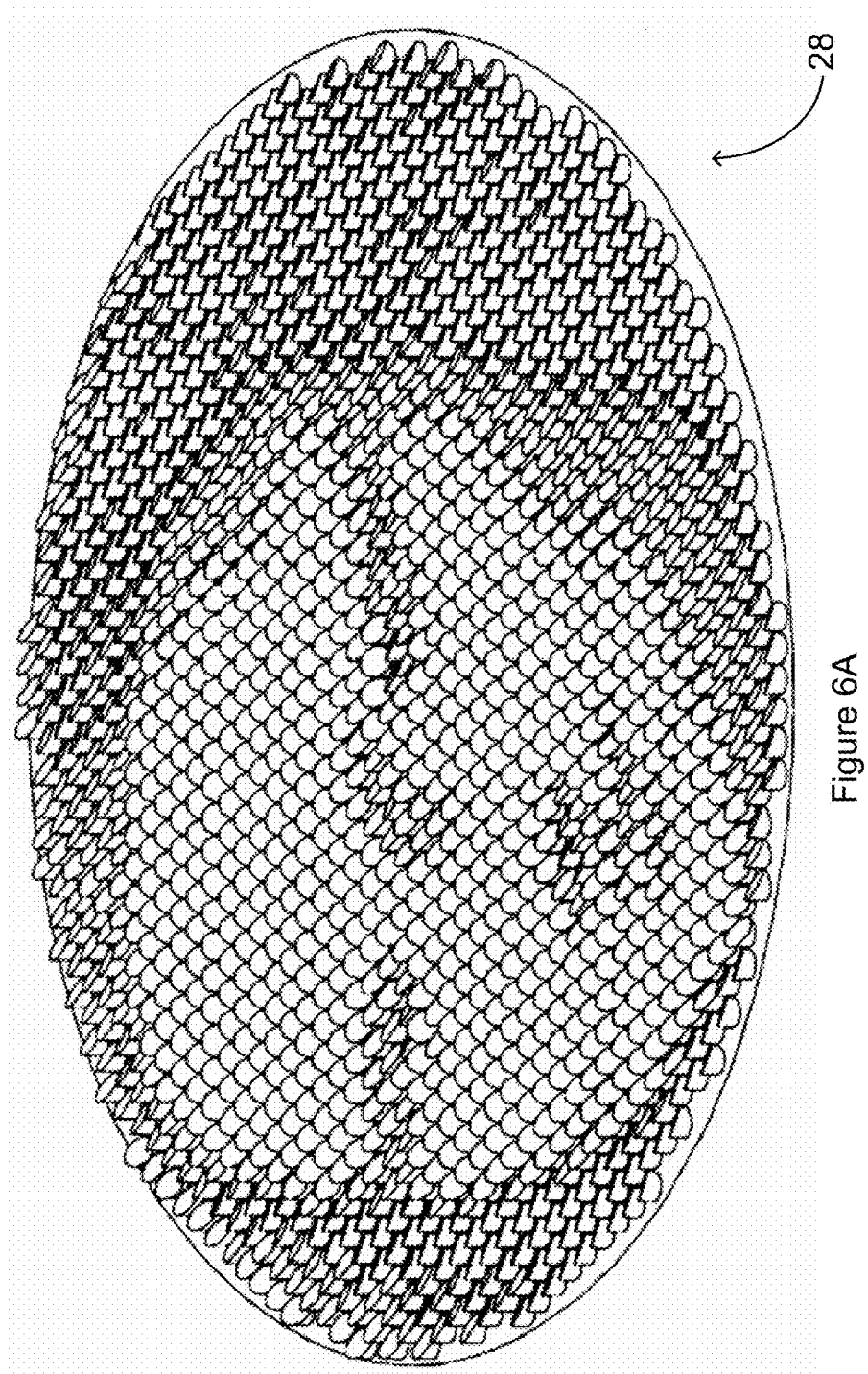
FIGS. 6A to 6C show a structure according to another embodiment of the invention from different viewing angles.
Figure 6B:
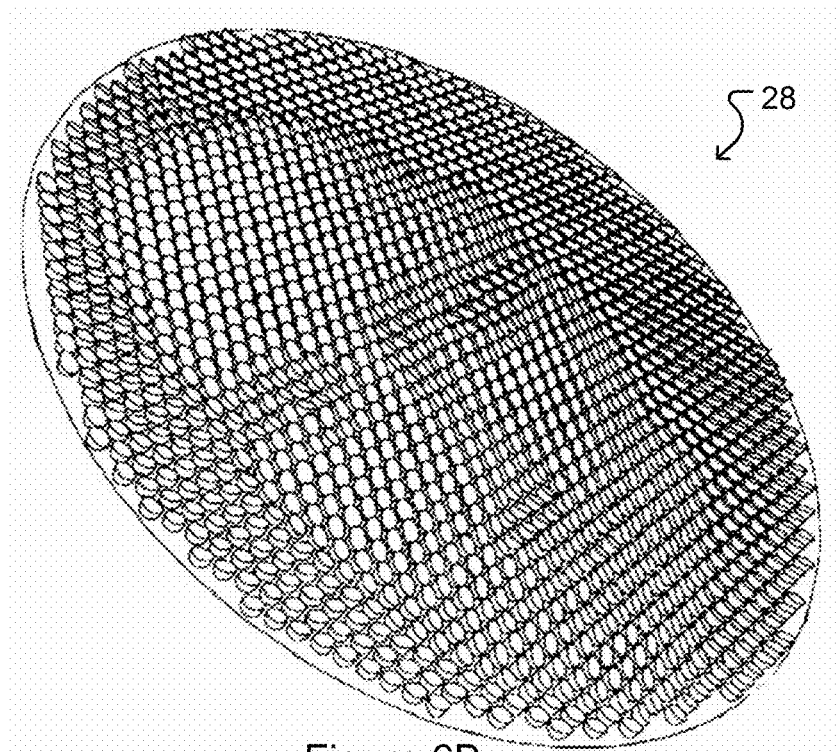
Figure 6C:
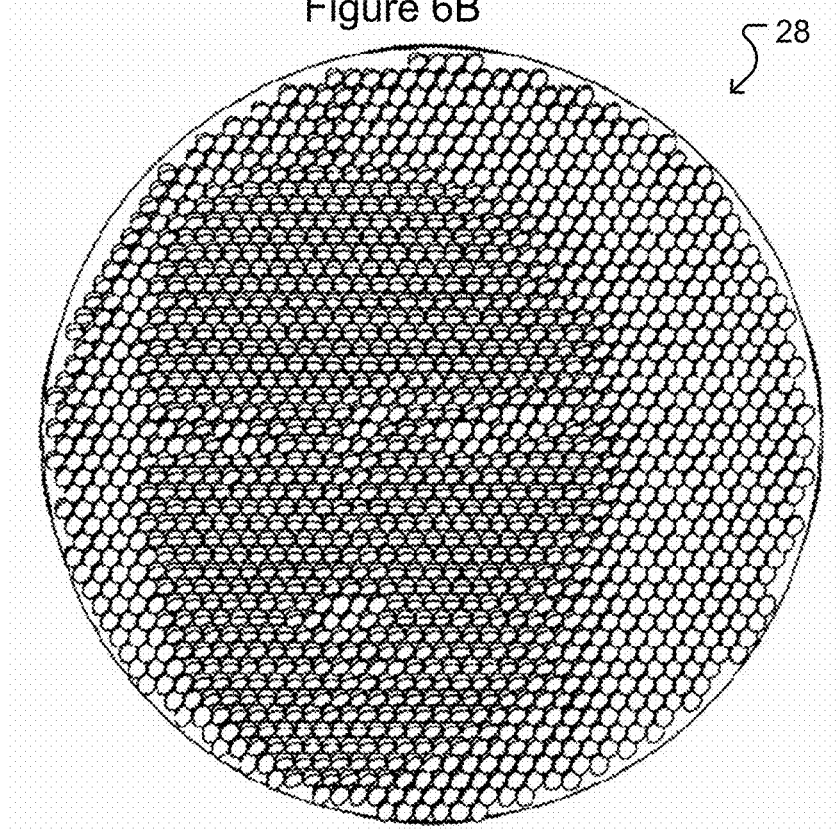

For example, FIGS. 6A to 6C show a structure 28 according to another embodiment of the invention from different viewing angles. Structure 28 comprises a generally circular substrate having tile elements in the form of cylindrical protrusions which represent an image of the Mona Lisa, FIG. 6A shows structure 28 from a first acute viewing angle. FIG. 6B shows structure 28 from a second acute viewing angle. FIG. 6C shows structure 28 from a perpendicular viewing angle. It can be seen that the luminance values of the image represented by structure 28 are different from different viewing angles, due to differences in the relative amount of surface area of the tile elements facing the observer.

As another example, referring to FIGS. 1 and 2, region 14 would appear brighter when viewed from the right (i.e., from the direction in which surfaces 26 in region 14 are facing) and darker when viewed from the left (i.e., from the direction opposite to the direction in which surfaces 26 in region 14 are facing). Thus, when an observer passes by a structure such as structure 10, the observer is presented with an image having luminance characteristics which change as the observer moves, producing a striking visual effect.

Structures such as structure 10 may be illuminated with light from different light sources incident on the structures at different angles. The different light sources may emit different colours of light, such that the colours appear to mix together when viewed by an observer.

The visual effect produced by a structure such as structure 10 may be enhanced by applying coatings to substrate 20 and/or surfaces 26. For example, a flat or matte white coating may be applied to surfaces 26, and a dark coating may be applied to substrate 20. Alternatively, surfaces 26 may be covered with an iridescent or fluorescent coating. Other coatings which enhance, augment or alter reflectivity may also be used to cover substrate 20 and/or surfaces 26, and substrate 20 and/or surfaces 26 may themselves be constructed from materials which enhance, augment or alter reflectivity.

In another embodiment, a substantially non-reflective coating may be applied to substrate 20, and a substantially reflective coating may be applied to surfaces 26. In such an embodiment, structure 10 may be positioned to reflect light from a light source to project the image onto a screen or the like. Structure 10 may alternatively or additionally be positioned such that surfaces 26 reflect colour from the surrounding environment to the observer.

Figure 7:
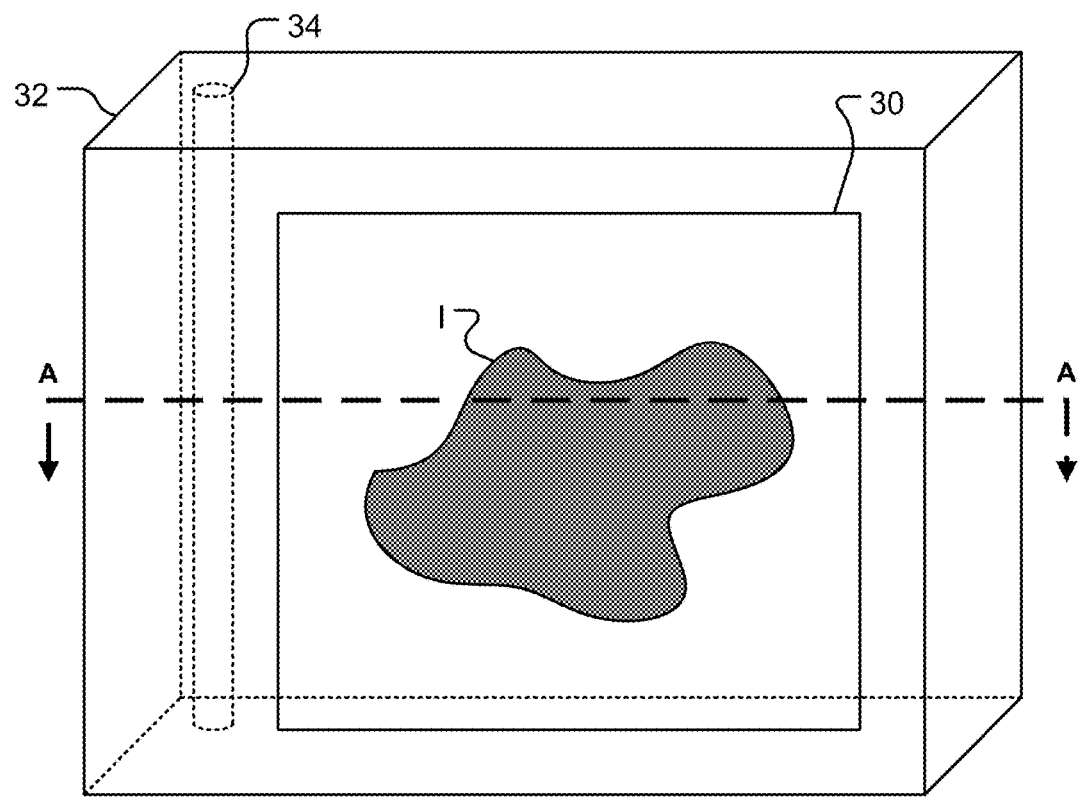
FIG. 7 schematically depicts a translucent structure coupled to a housing having a light source therein according to one embodiment of the invention.
Figure 7A:
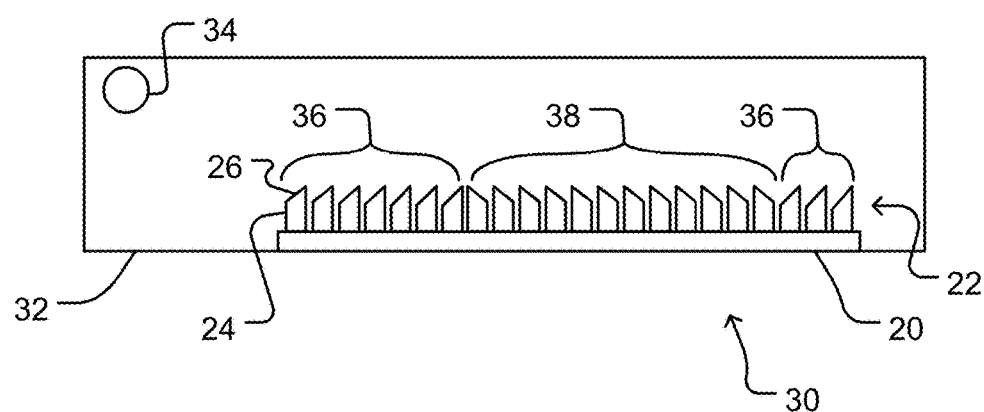
FIG. 7A is a sectional view taken along line A-A of FIG. 7.

Structures according to some embodiments of the invention may be constructed from translucent material and viewed from the back (i.e., the side opposite the one from which light is incident thereon). FIGS. 7 and 7A show an example of such a structure 30 used to represent an image I. Structure 30 is coupled to a housing 32 having a light source 34 therein. Structure 30 is constructed from a translucent material such as, for example, glass or acrylic. Areas of substrate 20 between tile elements may optionally be made opaque or covered with an opaque coating. In some embodiments it may be desirable to use a translucent material having an index of refraction of between 1 and 1.3. In other embodiments, translucent materials having higher indices of refraction may be selected.

Light from light source 34 is incident on surfaces 26 of tile elements 22 of structure 30, and is refracted by structure 30 to represent image I. Each tile element 22 corresponds to at least one pixel of image I. The orientation angle of each tile element 22 is selected such that light is incident on surface 26 at an angle of incidence which depends on characteristics (e.g., brightness) of the corresponding pixel of image I. For example, tile elements 22 which correspond to the brightest pixels of image I have an orientation angle of zero degrees (i.e., surfaces 26 face toward light source 34), and are collectively indicated by reference numeral 36 in FIG. 7A. Also, the inclination angles of tile elements 22 may vary depending on the distance from light source 34, with surfaces 26 farther away from light source 34 having a greater inclination angle than surfaces 26 closer to light source 34, such that the angle of incidence of light from light source 34 is relatively constant for all tile elements having an orientation angle of zero degrees. Tile elements 22 which correspond to the least bright pixels of image I have an orientation angle of 180 degrees (i.e., surfaces 26 face away from light source 34), and are collectively indicated by reference numeral 38 in FIG. 7A.

Structures such as structure 30 may be illuminated with light from different light sources incident on the structures at different angles. The different light sources may emit different colours of light, such that the colours appear to mix together when viewed by an observer.

Structure 10 or structure 30 may be constructed, for example, by machining a block of material to create cylindrical protrusions 24 and substrate 20. Then tile elements 22 may be formed by cutting cylindrical protrusions 24 according to the inclination and orientation angles assigned to tile elements 22 based on characteristics of the pixels of the image to be represented. Alternatively, structure 10 or structure 30 may be constructed by attaching pre-formed tile elements 22 to a substrate. In another example, structure 10 or structure 30 may be formed by constructing a mold and inserting a moldable material into the mold and allowing it to harden in the shape of structure 10 or structure 30.

Figure 8:
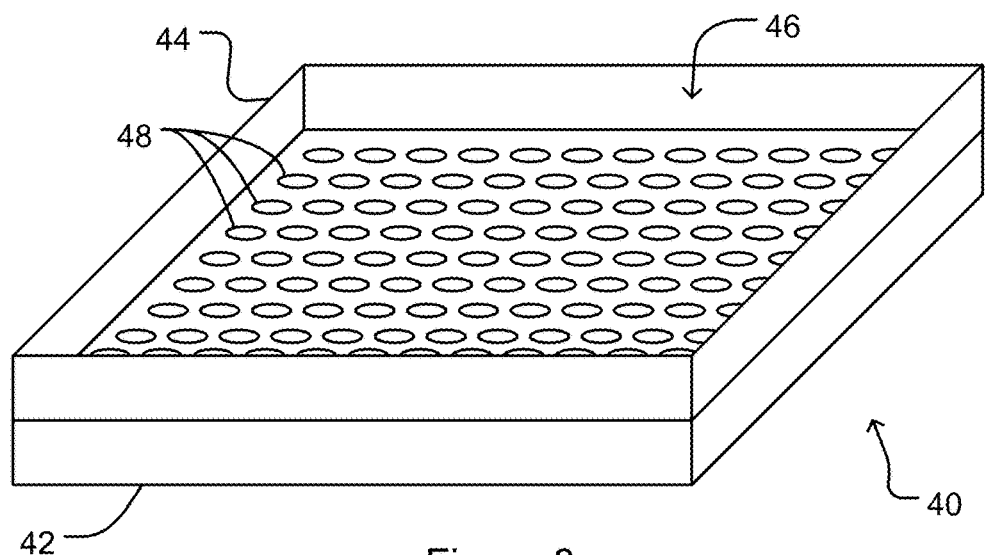
FIG. 8 shows an apparatus for making a structure for representing an image according to another embodiment of the invention.

FIG. 8 shows an apparatus 40 for forming a structure by molding, such as for example structure 10 or structure 30. Apparatus 40 comprises a base 42 and a wall 44 extending upwardly therefrom to define a volume 46. Base 42 has a plurality of recesses 48 therein. A moldable material may be introduced into volume 46 and allowed to harden to form a surface wherein tile elements 22 comprise protrusions 24 corresponding to recesses 48. The moldable material may be, for example, poured into the volume, pressed into the volume, or sucked into the volume by creating a reduced pressure in the volume.

Figure 9:
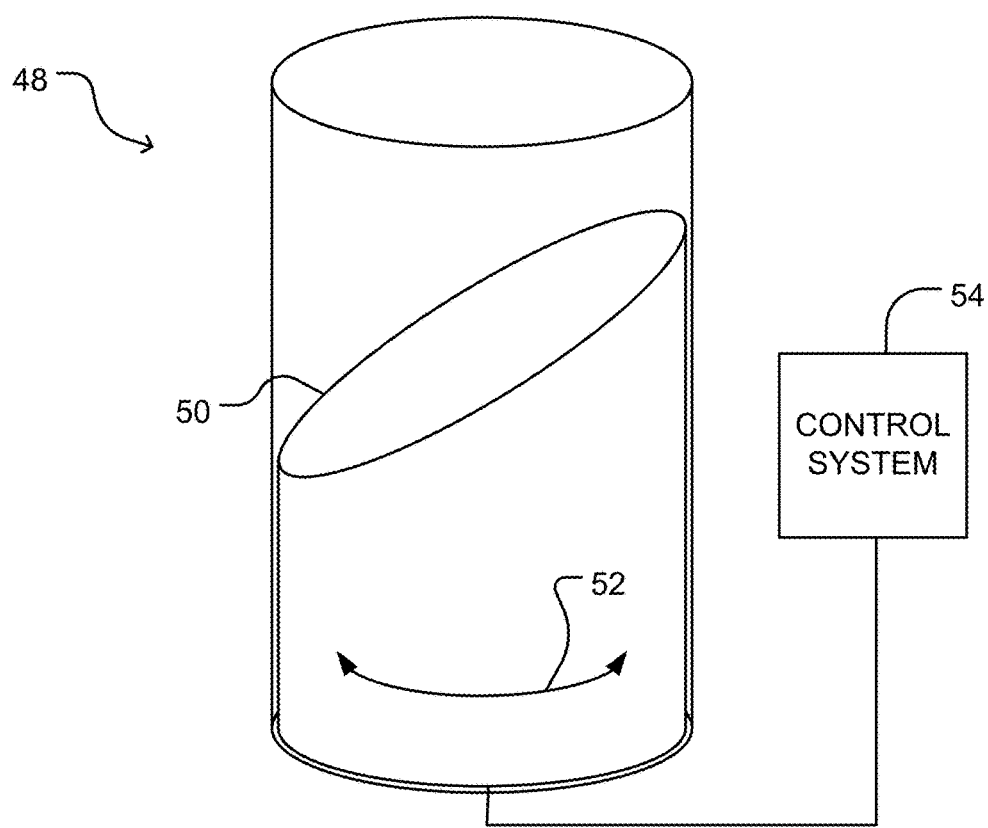
FIG. 9 shows one of the recesses of the apparatus of FIG. 8.
Figure 10:
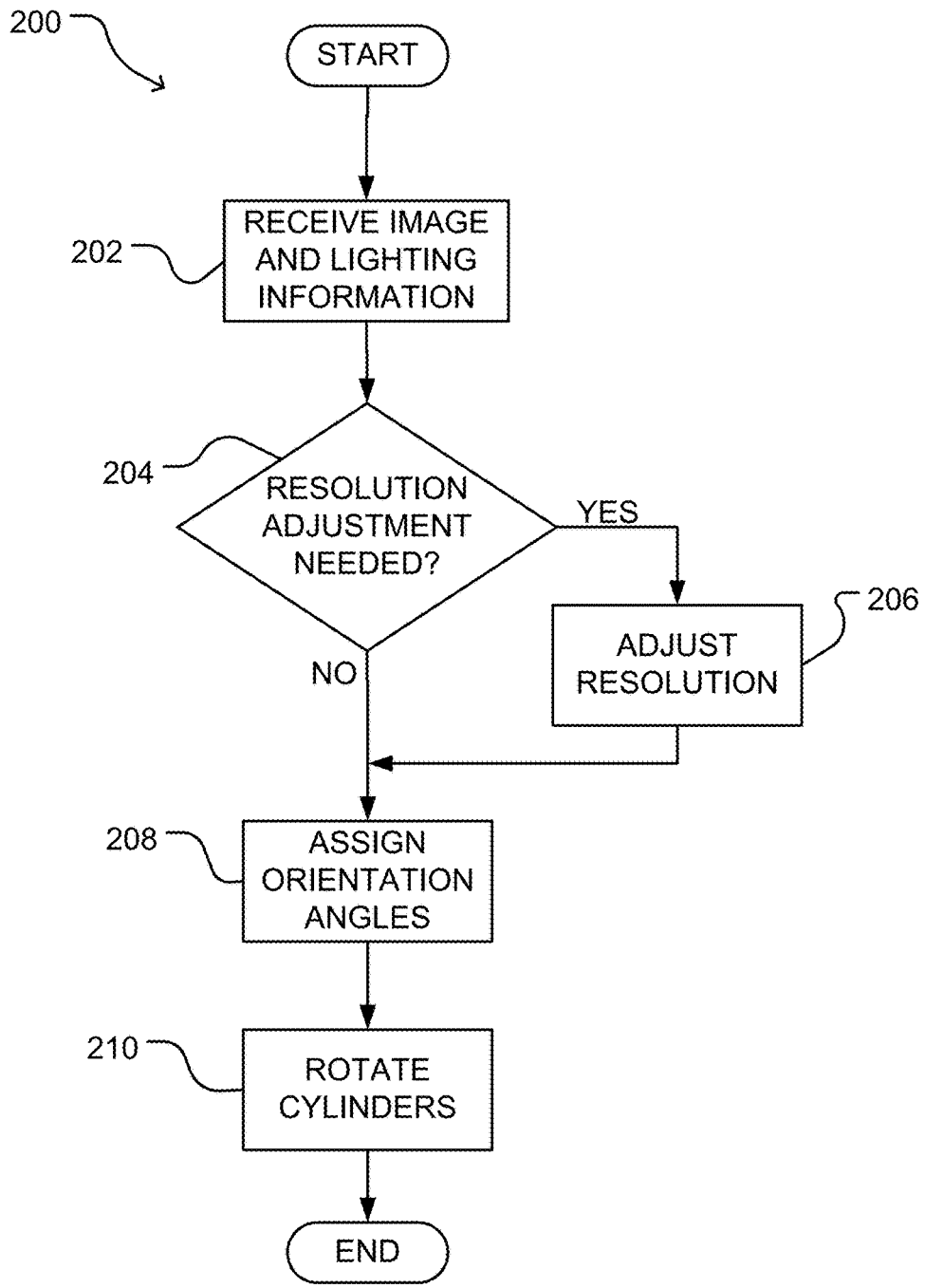
FIG. 10 is a flowchart illustrating a method of controlling the apparatus of FIG. 8.

FIG. 9 shows one of recesses 48 of FIG. 10. Recess 48 has a cylindrical plug 50 therein. Cylindrical plug 50 may be rotated as indicated by arrows 52 to select the orientation angle of tile element 22 formed in recess 48. The orientation of cylindrical plug 50 may be controlled by a control system 54. Control system 54 may be used to control the orientation of cylindrical plugs 50 in all of recesses 48 of FIG. 8.

FIG. 10 is a flow chart illustrating a method 200 which may be carried out by control system 54. At block 202 control system 54 receives an image to be represented by a structure to be formed with apparatus 40, and also receives information about the direction from which light will be incident of the structure to be formed. At block 204 control system 54 determines if the resolution of the image received at block 202 needs to be adjusted (i.e., if the image has a different number of pixels from the number of recesses 48). If the resolution needs to be adjusted (block 204 YES output) method 200 proceeds to block 206, where control system 54 adjusts the resolution of the image to match that of apparatus 40. If the image has a higher resolution than apparatus 40, the resolution of the image may be adjusted by grouping a plurality of pixels of the image together and calculating a single adjusted pixel from the plurality of pixels, such that there is one adjusted pixel for each recess 48. If the image has a lower resolution than apparatus 40, the resolution of the image may be adjusted by converting each pixel of the image into a plurality of adjusted pixels, such that there is one adjusted pixel for each recess 48.

If the resolution of the image does not need to be adjusted (block 204 NO output), or after the image resolution has been adjusted at block 206, method 200 proceeds to block 208 where control system 54 assigns orientation angles to the tile elements to be formed in recesses 48 based on characteristics of the corresponding pixels (or adjusted pixels) of the image. At block 210 control system 54 rotates cylindrical plugs 50 to orientations corresponding to the orientation angles assigned at block 208, and apparatus 40 is ready to receive the moldable material in volume 46. Apparatus 40 of FIG. 8 may be used, for example, in conjunction with thermo-plastic embossing or thermo-plastic molding techniques to introduce the moldable material into volume 46.

Figure 11:
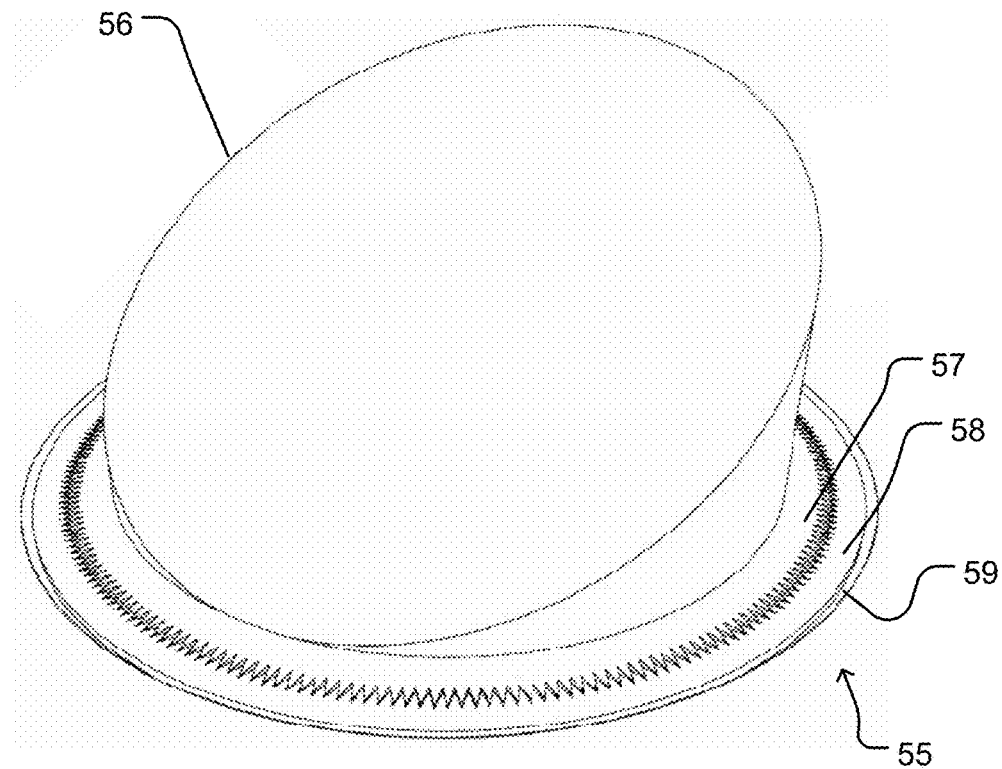
FIG. 11 shows a single tile element of a structure for representing an image according to another embodiment of the invention.
Figure 12:
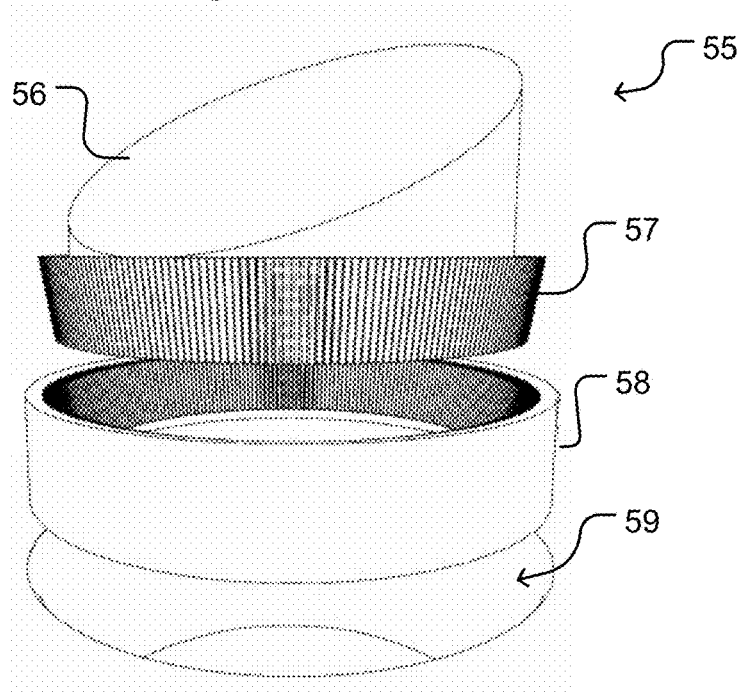
FIG. 12 is an exploded view of the tile element of FIG. 11.

FIGS. 11 and 12 show a tile element 55 according to another embodiment of the invention. Tile element 55 comprises a sheared cylinder 56 having a circumferentially toothed base 57. Toothed base 57 is received in an annular member 58 having correspondingly shaped teeth on the inside circumference thereof. Annular member 58 is inserted into a hole 59 in the substrate. The orientation angle of tile element 55 may be adjusted to select any one of a plurality of discrete values by inserting base 57 of sheared cylinder 56 into annular member 58 in any of one of a plurality of orientations permitted by inter-engagement of toothed base 57 and member 58.

Figure 13:
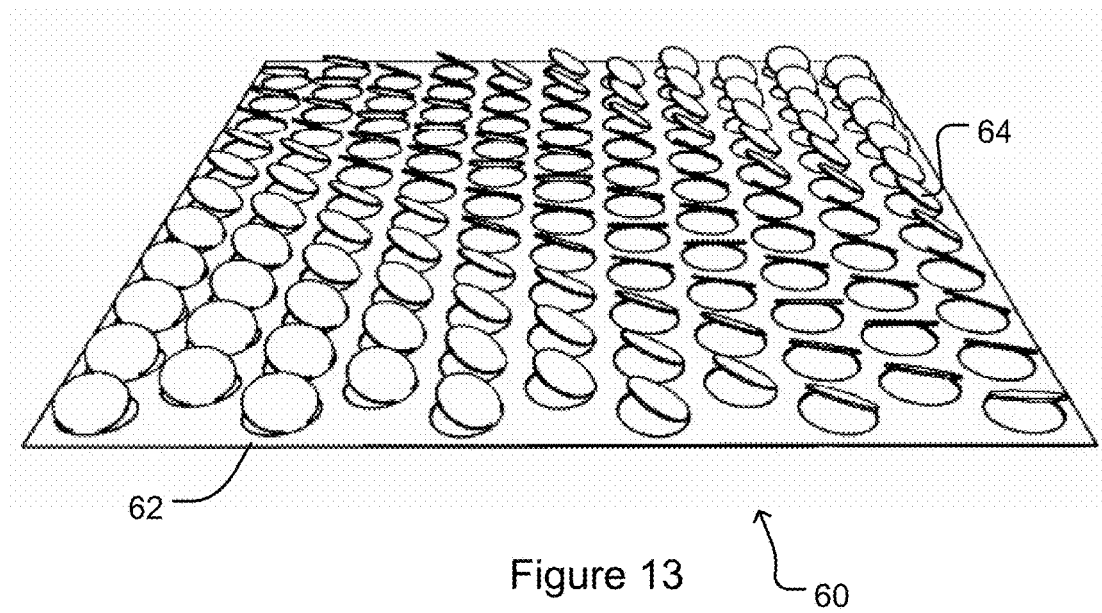
FIG. 13 shows a structure for representing an image according to another embodiment of the invention.

FIG. 13 shows a structure 60 according to another embodiment of the invention. In structure 60 the substrate comprises a sheet 62, and the tile elements comprise tabs 64 formed from sheet 62 and bent at the desired inclination and orientation angles. Structure 60 of FIG. 13 may also comprise graphic features (not shown). For example, sheet 62 may be printed or treated with a thermal overlay to form an image from pigment thereon, either before or after tabs 64 are formed from sheet.

Structures according to the invention need not necessarily comprise a substrate, so long as the tile elements are held in a controlled relationship to one another. Also, structures according to some embodiments of the invention could comprise a plurality of individual substrate elements which may be connected to one another.

Figure 14:
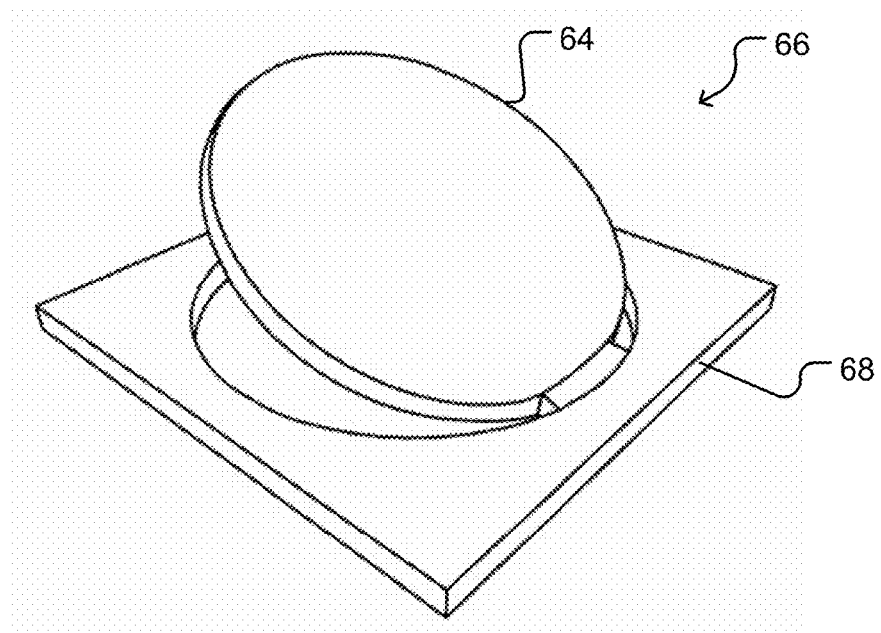
FIG. 14 shows a single tile element attached to an individual substrate element according to another embodiment of the invention.

FIG. 14 shows a single tile element 66 comprising a tab 64 formed from an individual substrate element 68. A plurality of tile elements 66 may be combined by joining their respective substrate elements 68 to form a structure such as structure 60 of FIG. 13.

Figure 15:
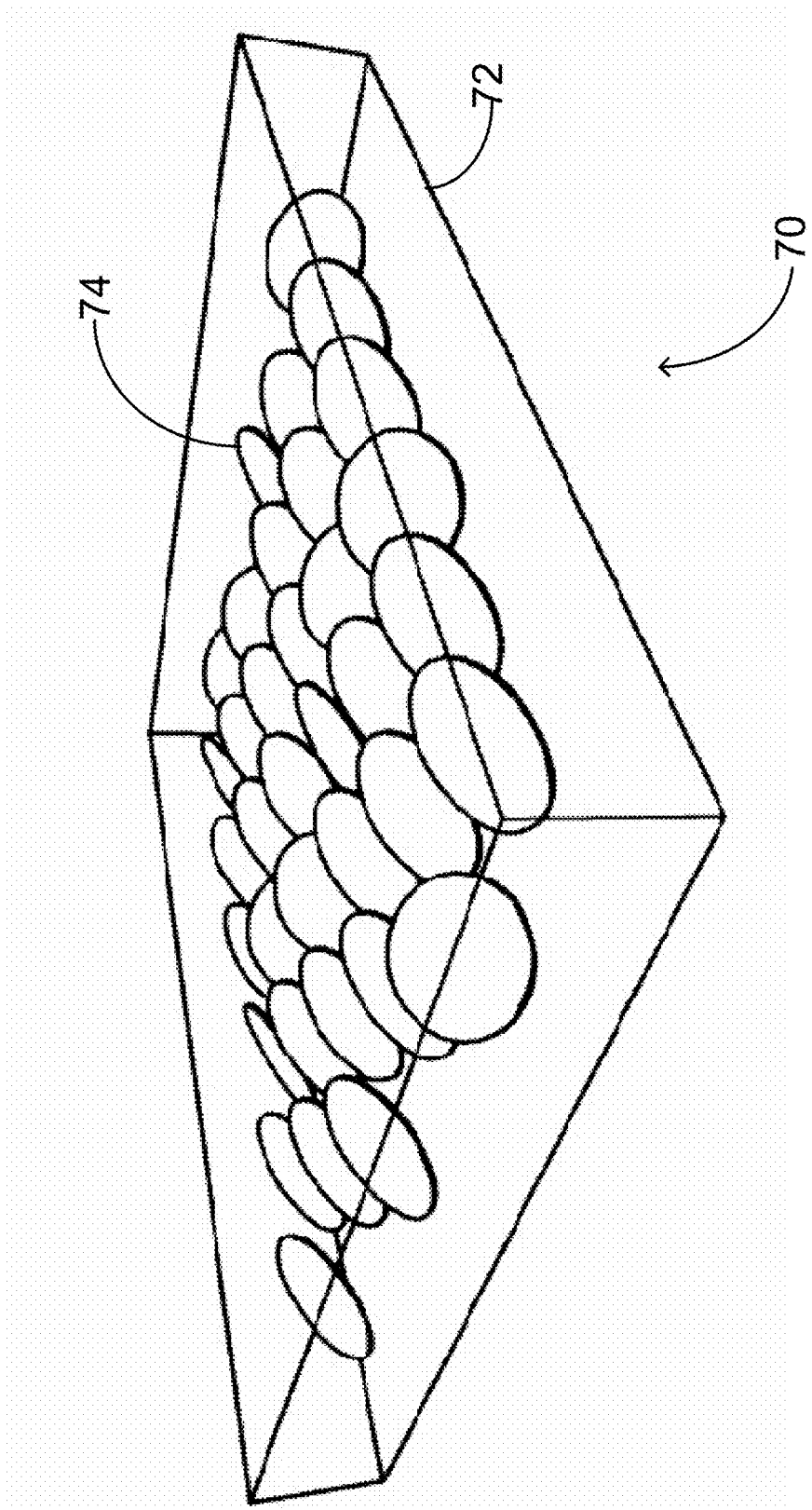
FIG. 15 shows a structure for representing an image according to another embodiment of the invention.

FIG. 15 shows a structure 70 according to another embodiment of the invention. In structure 70 the substrate comprises an optical medium 72, and the tile elements comprise regions 74 of interrupted transparency suspended in medium 72. Medium 72 may comprise a transparent material such as glass or acrylic, for example, Regions 74 may be formed, for example, by subsurface etching in medium 72. Alternatively, regions 74 could be formed by embedding opaque or partially opaque members in medium 72.

Figure 16:
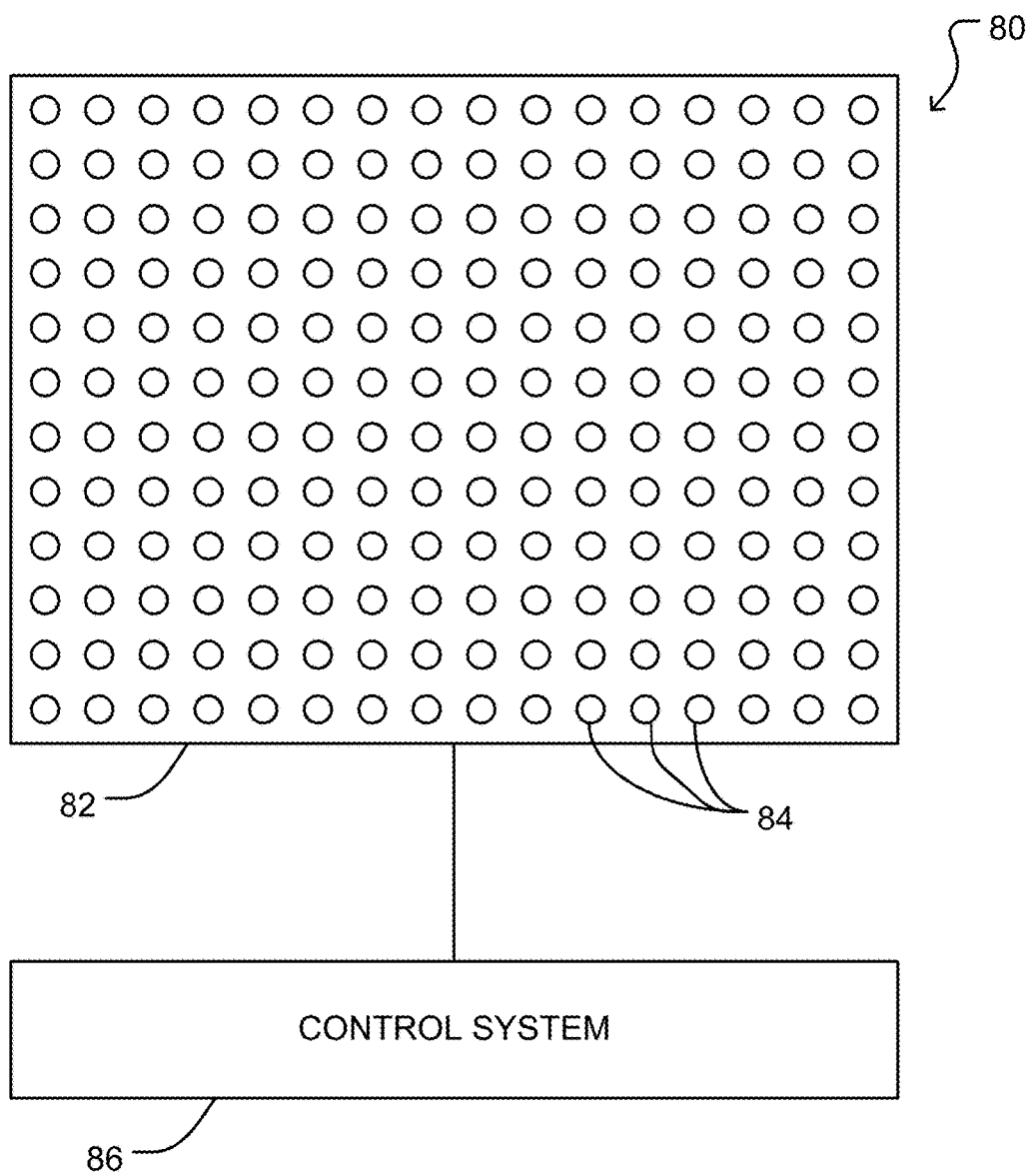
FIG. 16 shows a structure with active tile elements for representing dynamic images according to one embodiment of the invention.

FIG. 16 shows a dynamic structure 80 for representing dynamic images according to one embodiment of the invention. Structure 80 comprises a substrate 82 having a plurality of active tile elements 84 coupled thereto. Active tile elements 84 are operably connected to a control system 86 such that the orientation angle of each active tile element 84 can be dynamically controlled by control system 86. In some embodiments, control system 86 can also dynamically control the inclination angles of active tile elements 84. Control system 86 provides power and control signals to structure 80. In the illustrated embodiment, control system 86 is connected to structure 80 by means of a cable, control system 86 could alternatively communicate with structure 80 by wireless means, and structure 80 could receive power from solar panels.

Figure 17:
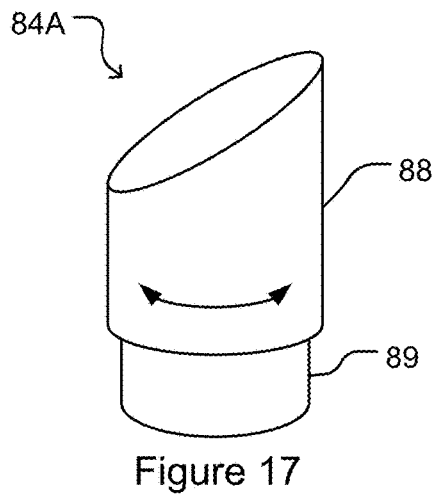
FIG. 17 shows an active tile element according to one embodiment of the invention.

FIG. 17 shows an example active tile element 84A according to one embodiment of the invention. Active tile element 84A comprises a sheared cylinder 88 coupled to a rotary actuator 89. Rotary actuator 89 may be coupled to substrate 82 (not shown in FIG. 17). Rotary actuator 89 adjusts the orientation angle of active tile element 84A by rotating sheared cylinder 88 under the control of control system 86 (not shown in FIG. 17).

Figure 18:
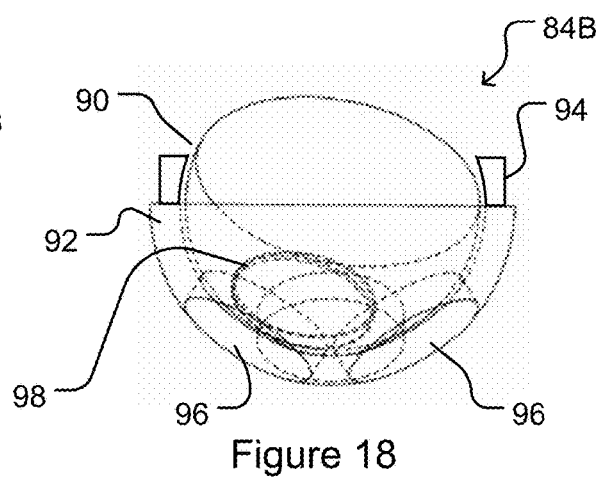
FIG. 18 shows an active tile element according to another embodiment of the invention.
Figure 19:
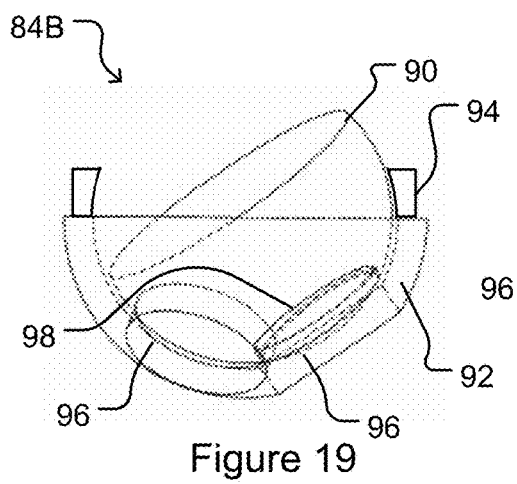
FIG. 19 is a rear view of the active tile element of FIG. 18.
Figure 20:
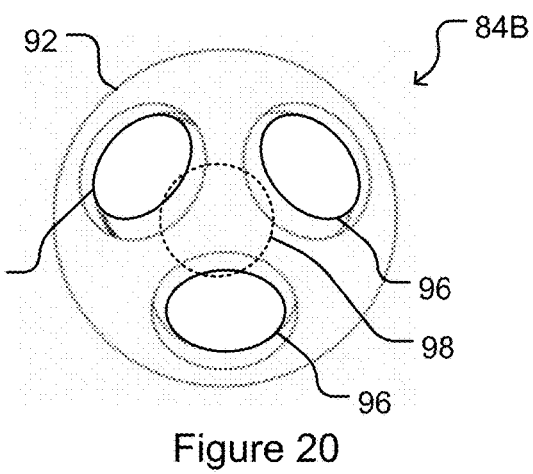
FIG. 20 is a bottom view of the active tile element of FIG. 18.

FIGS. 18 to 20 show an example active tile element 84B according to another embodiment of the invention. Active tile element 84B comprises a spherical section 90 positioned in a cup 92. Spherical section 90 is held in place by retaining means 94 attached to cup 92. For example, cup 92 may be a hemisphere having a radius slightly larger than the radius of spherical section 90, and retaining means 94 may comprise an aperture sized to fit over spherical section 90. Cup 92 has three coils 96 therein. Spherical section 90 has a magnet 98 therein, which may comprise a permanent or electro-magnet. Electric current is passed through coils 96 to create magnetic fields for adjusting the position of magnet 98 and therefore spherical section 90 under the control of control system 86 (not shown in FIGS. 18 to 20) to control the inclination and orientation angles of active tile element 84B.

Figure 21:
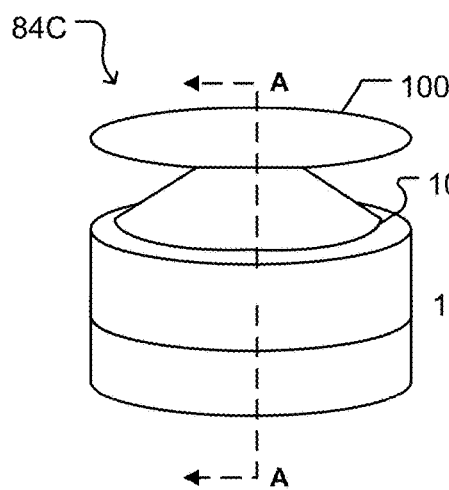
FIG. 21 shows an active tile element according to another embodiment of the invention.
Figure 22:
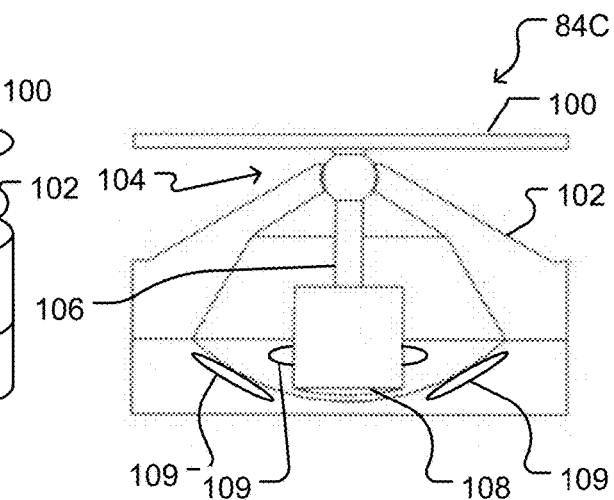
FIG. 22 is a sectional view taken along line A-A of FIG. 21.

FIGS. 21 and 22 show an example active tile element 84C according to another embodiment of the invention. Active tile element 84O comprises a platform 100 pivotally mounted on a hollow base 102 by means of a ball joint 104. Platform 100 has a shaft 106 attached thereto. A magnet 108 is attached to the end of shaft 106 opposite platform 100. Magnet 108 may comprise a permanent or electro-magnet. Base 102 has three coils 109 therein. Electric current is passed through coils 109 to create magnetic fields for adjusting the position of magnet 108 and therefore platform 100 under the control of control system 86 (not shown in FIGS. 21 and 22) to control the inclination and orientation angles of active tile element 84O.

Figure 23:
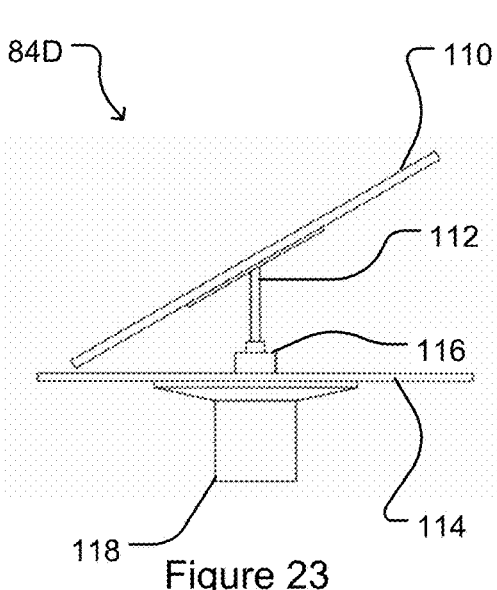
FIG. 23 shows an active tile element according to another embodiment of the invention.
Figure 24:
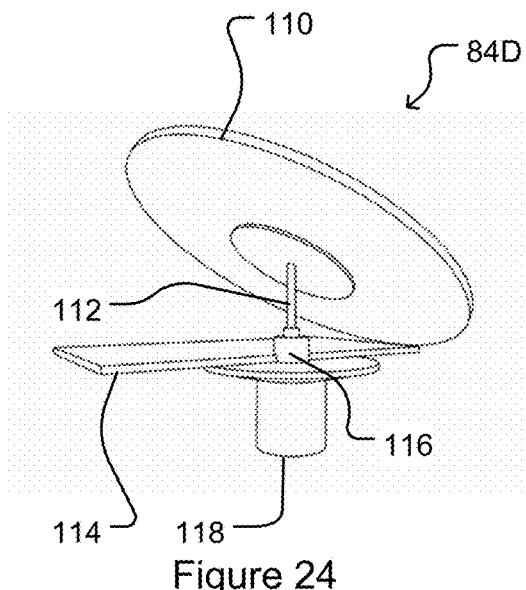
FIG. 24 is a bottom perspective view of the active tile element of FIG. 23.

FIGS. 23 and 24 show an example active tile element 84D according to another embodiment of the invention. Active tile element 84D comprises a platform 110 attached to a shaft 112. The inclination angle of active tile element 84D is fixed. Shaft 112 is rotatably coupled to a substrate element 114 by coupling means 116. The end of shaft 112 opposite platform 110 is coupled to a rotary actuator 118. Rotary actuator 118 rotates shaft 112 and therefore platform 110 under the control of control system 86 (not shown in FIGS. 23 and 24) to control the orientation angle of active tile element 84D.

Figure 25:
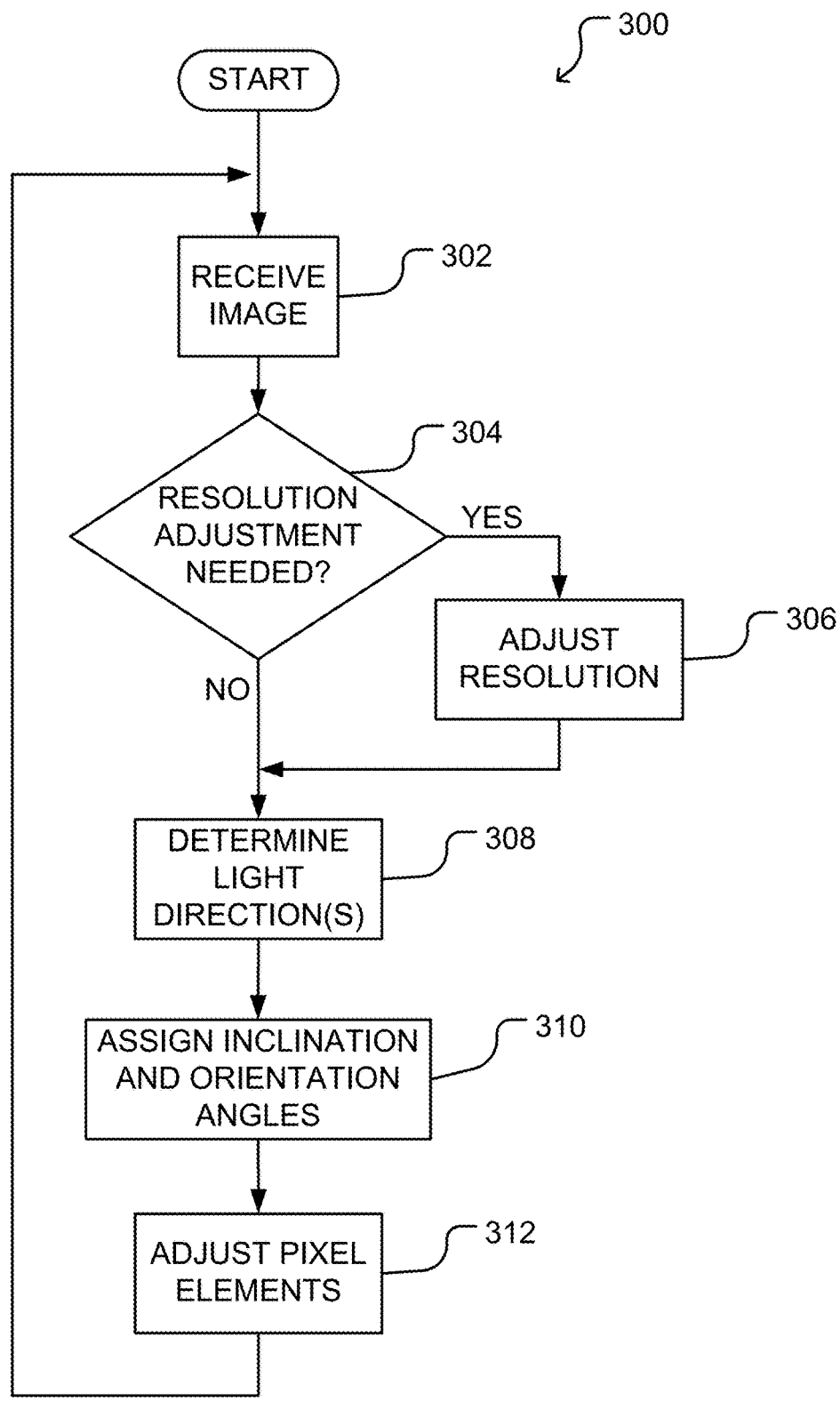
FIG. 25 is a flowchart illustrating a method of controlling the structure with active tile elements of FIG. 16.

FIG. 25 is a flowchart illustrating a method 300 carried out by control system 86 of FIG. 16 for controlling active tile elements 84 of structure 80. At block 302 control system 86 receives an image to be represented by structure 80. At block 304 control system 86 determines if the resolution of the image received at block 302 needs to be adjusted (i.e., if the image has a different number of pixels from the number of tile elements 84). If the resolution needs to be adjusted (block 304 YES output) method 300 proceeds to block 306, where control system 86 adjusts the resolution of the image to match that of structure 80. If the image has a higher resolution than structure 80, the resolution of the image may be adjusted by grouping a plurality of pixels of the image together and calculating a single adjusted pixel from the plurality of pixels, such that there is one adjusted pixel for each tile element 84. If the image has a lower resolution than structure 80, the resolution of the image may be adjusted by converting each pixel of the image into a plurality of adjusted pixels, such that there is one adjusted pixel for each tile element 84.

If the resolution of the image does not need to be adjusted (block 304 NO output), or after the image resolution has been adjusted at block 306, method 300 proceeds to block 308 where control system 86 determines the direction (or directions, if structure 80 is illuminated by more than one light source) from which light is incident on structure 80. Control system 86 may determine the direction(s) from which light is incident on structure 80 by receiving information from a light sensor. Alternatively or additionally, in situations where structure 80 is located outside, control system 86 may be programmed to determine the direction(s) from which light is incident on structure 80 based on the time of day.

At block 310 control system 86 assigns orientation angles to active tile elements 84 based on characteristics of the corresponding pixels of the image received at block 302. At block 312 control system 86 adjusts active tile elements 84 to the orientation angles assigned at block 310, and then method returns to block 302 to receive a new image.

Figure 26:
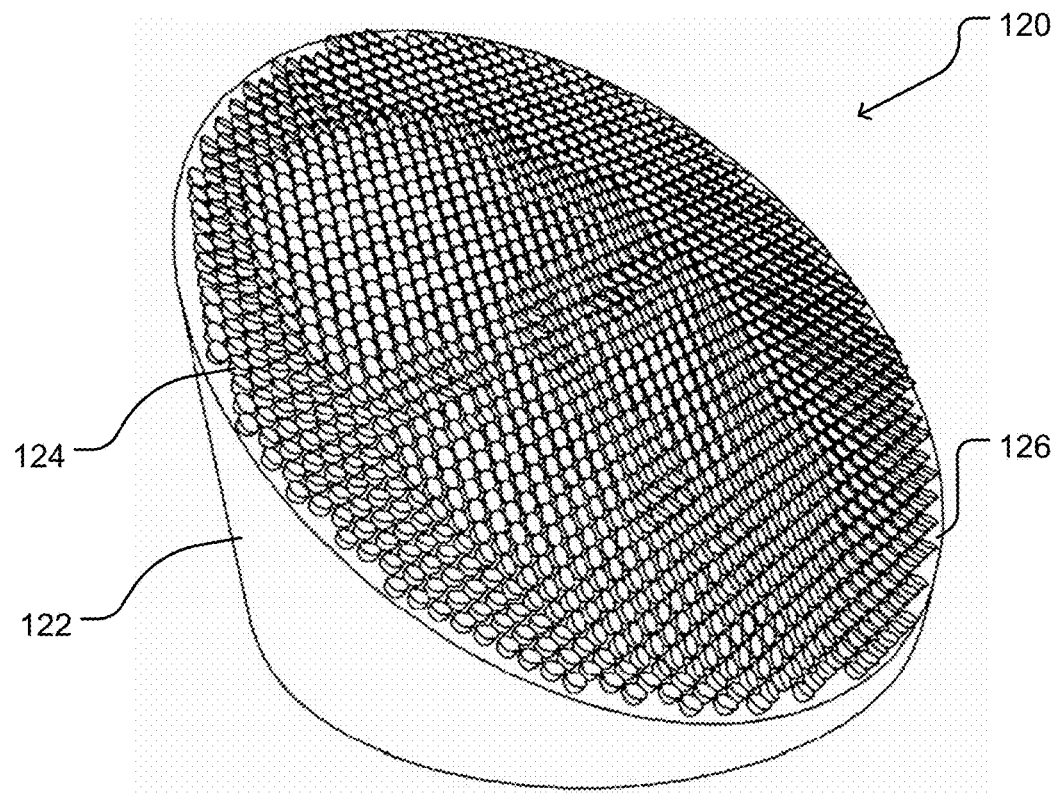
FIG. 26 shows a tile element having a plurality of smaller tile elements formed thereon according to another embodiment of the invention.
Figure 27:
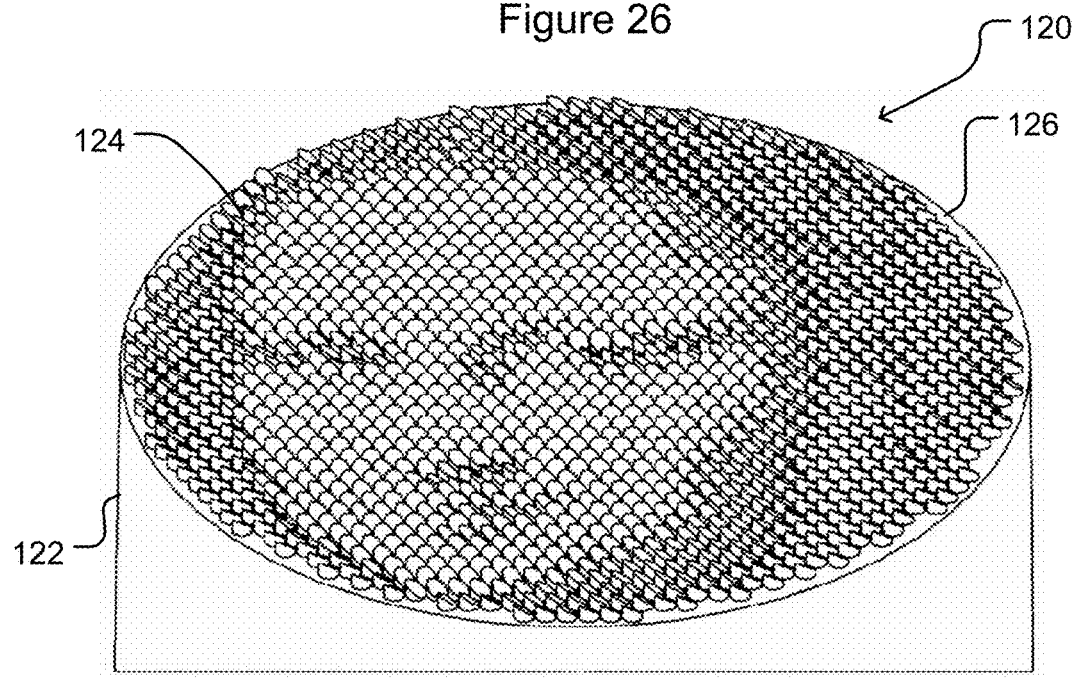
FIG. 27 is a front view of the tile element of FIG. 26.

FIGS. 26 and 27 show a tile element 120 according to another embodiment of the invention. Tile element 120 comprises a sheared cylinder 122 having a plurality of smaller tile elements 124 on a surface 126 thereof, Smaller tile elements 124 may be used to represent an image on surface 126, such as the Mona Lisa in the illustrated embodiment.

Figure 28:
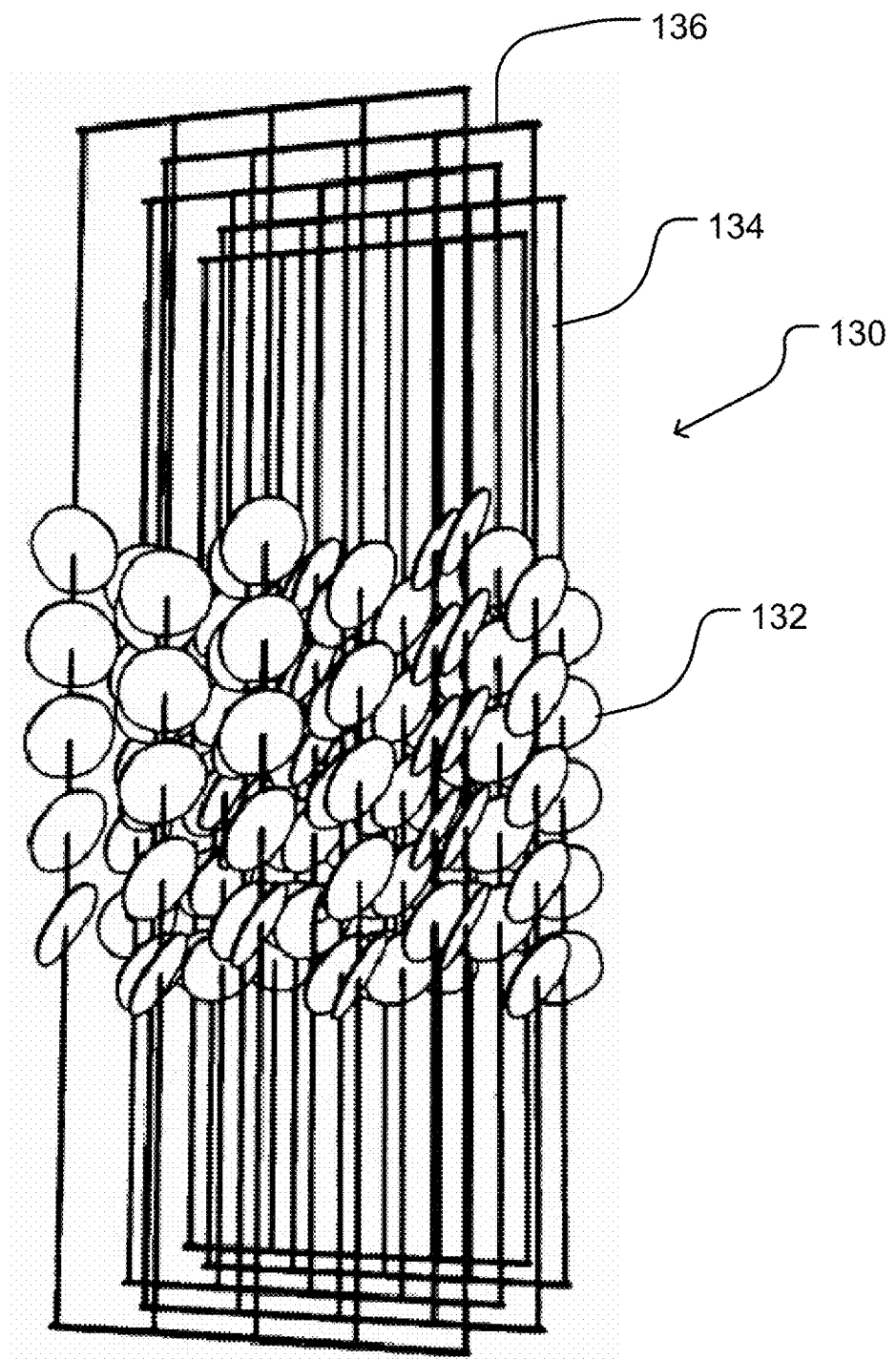
FIG. 28 shows a three dimensional array of tile elements according to another embodiment of the invention.

FIG. 28 shows a three dimensional array 130 according to another embodiment of the invention. Three dimensional array 130 comprises a plurality of tile elements 132 suspended on lines 134 such that tile elements 132 are held in a controlled relationship to one another. Lines 134 are arranged in rows 136, with tile elements 132 of each row 136 being used to represent a two dimensional slice of a three dimensional image. Tile elements 132 may have varying levels of transparency, with tile elements 132 near the middle of array 130 being the least transparent, and those near the edges of array 130 being the most transparent. Alternatively, tile elements 132 may all have the same level of transparency.

As will be apparent to those skilled in the art in the light of the foregoing disclosure, many alterations and modifications are possible in the practice of this invention. For example:

In the illustrated embodiments the tile elements have circular or elliptical surfaces, but the surfaces could have different shapes. However, circular and elliptical surfaces provide for a smoother looking image, particularly when the observer moves between different viewing locations.

In most of the illustrated embodiments the substrates are rectangular, but the substrates could have any shape.

In the illustrated embodiments the substrates are all generally planar, but the substrates could be non-planar.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A structure for representing a visual pattern, the structure comprising:
   a plurality of tile elements held in a fixed relationship to one another, each of the tile elements representing a corresponding area of the visual pattern, each of the tile elements comprising a generally planar surface inclined at an inclination angle with respect to a reference plane, each of the tile elements having an orientation angle with respect to a reference direction, the orientation angle defined between projections, on the reference plane, of a line normal to the generally planar surface and a line parallel to the reference direction;

wherein the orientation angle of each tile element is determined by a brightness of the corresponding area of the visual pattern, wherein the tile elements representing areas of the visual pattern with different brightnesses have different orientation angles, and wherein the tile elements reflect light incident thereon to present a pattern of luminance characteristics which varies based on a viewing location of an observer.

2. A structure according to claim 1 further comprising a substrate having a surface, wherein the plurality of tile elements are coupled to the surface of the substrate.

3. A structure according to claim 2 wherein the substrate comprises a sheet and each tile element comprises a tab formed from the sheet.

4. A structure according to claim 2 wherein each tile element comprises a protrusion projecting from the surface of the substrate.

5. A structure according to claim 4 wherein each protrusion is cylindrical.

6. A structure according to claim 2 wherein the surface of the substrate is substantially non-reflective and the generally planar surface of each tile element is substantially reflective.

7. A structure according to claim 2 wherein the substrate is non-planar.

8. A structure according to claim 1 wherein all of the tile elements have the same inclination angle.

9. A structure according to claim 1 wherein the generally planar surface of each tile element has a generally circular or elliptical shape.

10. A structure according to claim 1 wherein the generally planar surface of each tile element has a matte white coating.

11. A structure comprising:
   a substrate having a surface; and
   a plurality of tile elements coupled to the surface of the substrate and held in a fixed relationship to one another, each of the tile elements representing a corresponding area of the visual pattern, each of the tile elements comprising a generally planar surface inclined at an inclination angle with respect to the surface of the substrate, and having an orientation angle with respect to a reference direction, the orientation angle defined between projections, on the surface of the substrate, of a line normal to the generally planar surface and a line parallel to the reference direction;
wherein the orientation angle of each tile element is determined by a brightness of the corresponding area of the visual pattern, and
wherein the tile elements representing areas of the visual pattern with different brightnesses have different orientation angles.

12. A structure according to claim 11 wherein the tile elements reflect light incident thereon to present luminance characteristics which vary based on a viewing location of an observer.

13. A structure according to claim 11 wherein the substrate comprises a sheet and each tile element comprises a tab formed from the sheet.

14. A structure according to claim 11 wherein all of the tile elements have the same inclination angle.

15. A structure according to claim 11 wherein the generally planar surface of each tile element has a generally circular or elliptical shape.

16. A method for representing a visual pattern, the method comprising:
   providing a plurality of tile elements, each of the plurality of tile elements corresponding to an area of the visual pattern and having a generally planar surface; and,
   orienting each tile element such that the generally planar surface is inclined at an inclination angle with respect to a reference plane, and such that a projection of a line normal to the generally planar surface on the reference plane and a reference direction define an orientation angle, wherein the orientation angle of each tile element is determined by a brightness of the corresponding area of the visual pattern,
   wherein the tile elements representing areas of the visual pattern with different brightnesses have different orientation angles, and
   wherein the tile elements reflect light incident thereon to present a pattern of luminance characteristics which varies based on a viewing location of an observer.

17. A method according to claim 16 wherein providing the plurality of tile elements comprises forming the tile elements on a surface of a substrate.

18. A method according to claim 17 wherein orienting each tile element comprises assigning a value within the range of −180 to +180 degrees as the orientation angle for each tile element, wherein tile elements for which the desired brightness of the corresponding area of the visual pattern is highest have a value of 0 degrees assigned as the orientation angle and tile elements for which the desired brightness of the corresponding area of the visual pattern is lowest have a value of −180 degrees assigned as the orientation angle.

19. A structure for representing an image having a plurality of image areas, each image area having a brightness, the structure comprising:
   a substrate having a surface; and
   a plurality of tile elements formed on the surface of the substrate, each of the tile elements associated with one of the image areas, each of the tile elements comprising a generally planar surface inclined at an inclination angle with respect to the surface of the substrate, and having an orientation angle with respect to a reference direction, the orientation angle defined between projections, on the surface of the substrate, of a line normal to the generally planar surface and a line parallel to the reference direction;
   wherein the orientation angle of each tile element is determined by the brightness of the associated image area, and
   wherein the tile elements associated with image areas with different brightnesses have different orientation angles.

* * * * *